United States Patent

Lewis et al.

(10) Patent No.: US 8,362,075 B2
(45) Date of Patent: Jan. 29, 2013

(54) CYCLOHEXYL SULPHONES FOR TREATMENT OF CANCER

(75) Inventors: Huw David Lewis, Sawbridgeworth (GB); Timothy Harrison, Belfast (IE); Mark Steven Shearman, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 802 days.

(21) Appl. No.: 11/920,445

(22) PCT Filed: May 16, 2006

(86) PCT No.: PCT/GB2006/050107
§ 371 (c)(1),
(2), (4) Date: Jun. 8, 2010

(87) PCT Pub. No.: WO2006/123182
PCT Pub. Date: Nov. 23, 2006

(65) Prior Publication Data
US 2010/0267801 A1    Oct. 21, 2010

(30) Foreign Application Priority Data

May 17, 2005  (GB) .................................. 0509929.6
Oct. 24, 2005  (GB) .................................. 0521538.9

(51) Int. Cl.
*A61K 31/235*    (2006.01)
(52) U.S. Cl. ..................................... 514/532; 514/237.5
(58) Field of Classification Search .................. 514/532, 514/237.5
See application file for complete search history.

(56) References Cited

U.S. PATENT DOCUMENTS 7,799,782 B2 *  9/2010  Munson et al. ............ 514/234.5
2002/0151487 A1  10/2002  Nickoloff et al.

FOREIGN PATENT DOCUMENTS

| WO | WO03/018543 | 3/2003 |
| WO | WO2004/013090 | 2/2004 |
| WO | WO2004/073630 | 9/2004 |
| WO | WO 2006/001956 | 1/2006 |
| WO | WO2006/015375 | 2/2006 |
| WO | WO2006/052128 | 5/2006 |

OTHER PUBLICATIONS

Tarassishin, L et al., PNAS, vol. 101(49), pp. 17050-17055, "Processing of Notch and amyloid precursor protein by γ-secretase in spatially distinct", 2004.
Nickoloff, BJ et al., Oncogen, vol. 22, pp. 6598-6608 (2004), "Notch signaling as a therapeutic target in cancer: a new approach to the development of cell fate modifying agents".
McKenzie, GJ et al., Expert Opinion on Therapeutic Targets, vol. 9(2), pp. 395-410 (2005), "Notch: a unique therapeutic target for immunomodulation".
Qin, JZ et al., Molecular Cancer Therapeutics, vol. 3(8), pp. 895-902 (2004), "p53-independent NOXA induction overcomes apoptotic resistance of malignant melanomas".
van Es, JH et al., Nature, vol. 435, pp. 959-963 (2005), "Notch/γ-secretase inhibition turns proliferative cells in intestinal crypts and adenomas into goblet cells".
Callahan, R et al., Journal of Mammary Gland Biology and Neoplasia, vol. 9(2), pp. 145-163 (2004), "Notch signaling in mammary development and oncogenesis".
Collins, BJ et al., Seminars in Cancer Biology, vol. 14, pp. 357-364 (2004), "Notch in lung development and lung cancer".
Axelson, H, Seminars in Cancer Biology, vol. 14, pp. 317-319 (2004), "Notch signaling and cancer: emerging complexity".
Zweidler-McKay, PA et al., Seminars in Cancer Biology, vol. 14, pp. 329-340 (2004), "Notch and T cell malignancy".
Weng, AP et al., Molecular and Cellular Biology, vol. 23(2), pp. 655-664 (2003), "Growth suppression of pre-T acute lymphoblastic leukemia cells by inhibition of notch signaling".
Allenspach, EJ et al., Cancer Biology & Therapy, vol. 1(5), pp. 466-476 (2002), "Notch signaling in cancer".
Weng, AP et al., Science, vol. 306, pp. 269-271 (2004), "Activating mutations of Notch 1 in human T cell acute lymphoblastic leukemia".
Curry, et al., Oncogen, vol. 24, pp. 6333-6344 (2005), "Gamma secretase inhibitor blocks Notch activation and induces apoptosis in Kaposi's sarcoma tumor cells".

* cited by examiner

*Primary Examiner* — Rei-tsang Shiao
(74) *Attorney, Agent, or Firm* — Joan E. Switzer; David A. Muthard

(57) ABSTRACT

Sulphones of formula (I) are disclosed for use in treatment of cancer.

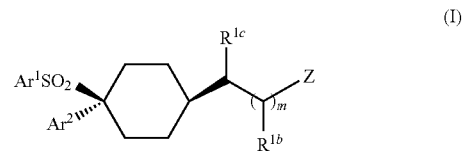

12 Claims, No Drawings

CYCLOHEXYL SULPHONES FOR TREATMENT OF CANCER

PRIORITY CLAIM

This application is a §371 National Stage Application of PCT/GB2006/050107, filed on May 16, 2006, which claims priority from GB 0509929.6, filed on May 17, 2005, and GB 0521538.9, filed on Oct. 24, 2005.

This invention relates to methods and materials for treatment of the human or animal body. In particular it relates to the use of a particular class of sulphones for treatment of cancer.

Notch signalling plays an important part in various cellular and developmental processes, including differentiation, proliferation, survival and apoptosis (Artavaris-Tsakonas et al, *Science* (1999), 284, 770-776). A significant body of evidence also indicates that augmented or abnormally-prolonged Notch signalling is involved in tumorigenesis (see, for example, Callahan and Egan, J. *Mammary Gland Biol. Neoplasia* (2004), 9, 145-163; Collins et al, *Semin. Cancer Biol.* (2004), 14, 357-64; Axelson, ibid. (2004), 14, 317-319; Zweidler-McKay and Pear, ibid (2004), 14, 329-340; and Weng et al, *Mol. Cell. Biol.* (2003), 23, 655-664).

Modified Notch1 signalling has been implicated in lymphoblastic leukemia/lymphomas, mammary gland tumors, lung cancer, neuroblastomas, skin cancer, cervical cancer, epithelial tumors and prostate cancer. (Allenspach. et. al., *Cancer Biology and Therapy*, (2002) 1:5, 466-476).

Activating mutations in Notch1 are implicated in human T Cell Acute Lymphoblastic Leukemia (T-ALL) (Weng, et al., *Science*, 306:269-271 (2004)).

Notch signalling is elicited by receptor-ligand interaction between neighbouring cells. As a result of the receptor-ligand interaction, the Notch protein undergoes intra-membrane proteolysis, releasing an intracellular fragment which migrates to the nucleus where it modulates gene expression.

In view of the involvement in tumorigenesis, there has been much interest in inhibition of Notch signalling as a method of treating malignancies. Various types of intervention in the signalling process have been considered, such as inhibiting expression of the Notch protein, blockade of the receptor to prevent ligand binding, and inhibition of the intra-membrane proteolysis. The last-named is particularly attractive because the enzyme complex responsible for the proteolysis, gamma-secretase, has been extensively studied in connection with the cleavage of other protein substrates, notably amyloid precursor protein (APP) which is implicated in Alzheimer's disease. Hence a large number of compounds have been identified which can be shown to inhibit the cleavage of APP by gamma-secretase in vitro. The relevant compounds typically show equivalent ability to inhibit the cleavage of Notch protein by gamma-secretase in vitro (see Lewis et al *Biochemistry* (2003), 42, 7580-7586). However, clinical studies using such compounds have been severely hampered by the discovery of serious gastro-intestinal (GI) toxicity (believed to be mechanism based) associated with this class of compound (Searfoss et al, *J. Bio. Chem.* (2003), 278, 46107-46116; Wong et al, ibid (2004), 279, 12876-12882).

It has now been unexpectedly found that a particular class of sulfone derivatives can provide significant inhibition of gamma-secretase in vivo without causing the GI toxicity seen previously with other gamma-secretase inhibitors. This valuable property renders the compounds suitable for use in treating disorders associated with Notch signalling activity, in particular cancer.

Therefore, in accordance with the invention there is provided the use, for the manufacture of a medicament for treating cancer, of a compound of formula I:

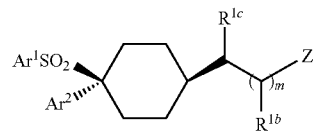

wherein:

m is 0 or 1;

Z represents CN, $OR^{2a}$, $CO_2R^{2a}$ or $CON(R^{2a})_2$;

$R^{1b}$ represents H, $C_{1-4}$alkyl or OH;

$R^{1c}$ represents H or $C_{1-4}$alkyl;

$Ar^1$ represents phenyl or pyridyl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents phenyl which is substituted in the 2- and 5-positions with halogen;

$R^{2a}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, $OR^{2b}$, $CO_2R^{2b}$, $N(R^{2b})_2$, $CON(R^{2b})_2$, Ar and COAr; or $R^{2a}$ represents Ar; or two $R^{2a}$ groups together with a nitrogen atom to which they are mutually attached may complete an N-heterocyclyl group bearing 0-4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

$R^{2b}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr; or $R^{2b}$ represents Ar; or two $R^{2b}$ groups together with a nitrogen atom to which they are mutually attached may complete an N-heterocyclyl group bearing 0-4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

Ar represents phenyl or heteroaryl bearing 0-3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl;

or a pharmaceutically acceptable salt thereof.

According to another aspect of the invention there is provided a method of treating a subject suffering from cancer comprising administering to that subject an effective amount of a compound of formula I as defined above, or a pharmaceutically acceptable salt thereof.

The subject is preferably a mammal, in particular a human.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl"$C_{1-6}$alkyl, "$C_{2-6}$alkynyl" and "$C_{1-6}$alkoxy" are to be construed in an analogous manner.

The expression "$C_{3-6}$cycloalkyl" as used herein refers to nonaromatic monocyclic or fused bicyclic hydrocarbon ring systems comprising from 3 to 6 ring atoms. Examples include cyclopropyl, cyclobutyl, cyclopentyl, cyclohexyl, and cyclohexenyl.

The expression "$C_{3-6}$ cycloalkyl$C_{1-6}$alkyl" as used herein includes cyclopropylmethyl, cyclobutylmethyl, cyclopentylmethyl and cyclohexylmethyl.

The expression "N-heterocyclyl" as used herein means a cyclic or polycyclic system of up to 10 ring atoms selected from C, N, O and S, wherein none of the constituent rings is aromatic and wherein at least one ring atom is nitrogen and bonding is through said ring nitrogen. Preferred N-heterocyclyl groups are monocyclic systems of 4-6 members, such as azetidinyl, pyrrolidinyl, piperidinyl, piperazinyl, morpholinyl, thiomorpholinyl, imidazolidinyl, oxazolidinyl and thiazolidinyl.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Preferred heteroaryl groups are monocyclic systems of 5 or 6 members such as pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups. Further examples of heteroaryl groups include tetrazole, 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts, but other salts may be useful in the preparation of the said compounds or of their pharmaceutically acceptable salts. Suitable pharmaceutically acceptable salts of the compounds include acid addition salts, such as those formed with hydrochloric, sulphuric, methanesulphonic, fumaric, maleic, succinic, acetic, benzoic, oxalic, citric, tartaric, carbonic or phosphoric acids, and, where the compounds carry an acidic moiety, sodium, potassium, calcium or magnesium salts, and salts formed with suitable organic ligands, e.g. quaternary ammonium salts or pyridinium salts.

Where the compounds useful in the invention have at least one asymmetric centre, they may accordingly exist as enantiomers. Where the compounds possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, certain compounds used in the invention may exist as enantiomers by virtue of the asymmetry of the molecule as a whole. It is to be understood that in such cases both enantiomers, and mixtures thereof in any proportion, are included within the scope of the invention, and that structural formulae depicting molecules of this type shall be representative of both of the possible enantiomers, unless otherwise indicated.

In the compounds of formula I, $Ar^1$ represents optionally substituted phenyl or pyridyl, in particular optionally substituted phenyl or 3-pyridyl. $Ar^1$ is preferably selected from phenyl groups substituted in the 4-position with halogen, methyl or trifluoromethyl and phenyl groups substituted in the 3- and 4-positions by halogen.

$Ar^1$ is preferably 2,5-difluorophenyl.

In particular embodiments, $Ar^1$ is 4-chlorophenyl or 4-trifluoromethylphenyl and $Ar^2$ is 2,5-difluorophenyl.

$R^{1b}$ typically represents H, methyl or OH, preferably H.

$R^{1c}$ typically represents H or methyl, preferably H.

When m is 1 $R^{1b}$ and $R^{1c}$ preferably do not both represent $C_{1-4}$alkyl.

Particular values of $R^{2a}$ include H, phenyl, pyridyl, $C_{3-6}$cycloalkyl (such as cyclopropyl, cyclobutyl and cyclopentyl), $C_{3-6}$cycloalkyl$C_{1-6}$alkyl (such as cyclopropylmethyl), $C_{2-6}$alkenyl (such as allyl), and linear or branched $C_{1-6}$alkyl which is optionally substituted with $CF_3$, Ar, $OR^{2b}$, $N(R^{2b})_2$, $CO_2R^{2b}$ or $CON(R^{2b})_2$.

Examples of N-heterocyclyl groups represented by $N(R^{2a})_2$ include piperidin-1-yl (optionally substituted with OH, $CO_2H$, $CO_2C_{1-4}$alkyl, Me or Ph), piperazin-1-yl (optionally substituted with Me or Ph), morpholin-4-yl, thiomorpholin-4-yl, 1,1-dioxo-thiomorpholin-4-yl, 2-oxo-imidazolidin-1-yl, 5,5-dimethyl-2,2-dioxo-oxazolidin-3-yl, 2-oxo-oxazolidin-3-yl, 2-oxo-pyridin-1-yl, and 2-oxo-pyrrolidin-1-yl.

$R^{2b}$ typically represents H or $C_{1-4}$alkyl.

When Z represents $OR^{2a}$, $R^{2a}$ aptly represents H, Ar (especially pyridyl), alkyl (such as methyl, ethyl, propyl or butyl), or substituted alkyl (especially $CH_2Ar$ such as benzyl or pyridylmethyl).

When Z represents $CO_2R^{2a}$, $R^{2a}$ aptly represents H or alkyl (such as methyl, ethyl, propyl or butyl).

When Z represents $CON(R^{2a})_2$, the $R^{2a}$ a groups independently represent H or optionally substituted alkyl, cycloalkyl, cycloalkylalkyl or alkenyl, or together complete an N-heterocyclyl group. Very aptly, one $R^{2a}$ a represents H and the other represents H, alkyl (such as methyl, ethyl, n-propyl, isopropyl, n-butyl, sec-butyl, tert-butyl or 1-ethylpropyl), alkenyl (such as allyl), cycloalkyl (such as cyclopropyl, cyclobutyl or cyclopentyl), cycloalkylalkyl (such as cyclopropylmethyl) or substituted alkyl (such as alkyl substituted with Ar, especially 2-pyridylethyl, 3-(imidazol-1-yl)propyl or 2-phenylethyl; or alkyl substituted with $CF_3$, $CO_2R^{2b}$, or $CON(R^{2b})_2$, especially 2,2,2-trifluoroethyl, methoxycarbonylmethyl or carbamoylmethyl). Alternatively, the two $R^{2a}$ a groups complete an N-heterocyclyl group, such as morpholine, thiomorpholine, thiomorpholine-1,1-dioxide, 4-methylpiperazine, 4-phenylpiperazine, piperidine, 4-hydroxypiperidine or piperidine which is substituted in the 3- or 4-position with $CO_2R^{2b}$ and/or $C_{1-4}$alkyl, especially 3- or 4-carboxypiperidine, 3- or 4-ethoxycarbonylpiperidine, 3-carboxy-3-methylpiperidine and 3-ethoxycarbonyl-3-methylpiperidine.

Particularly preferred compounds include those in which $R^{1b}$ and $R^{1c}$ are both H, and either m is 0 and Z is $CON(R^{2a})_2$ or m is 1 and Z is $CO_2R^{2a}$, where $R^{2a}$ has the definition and preferred identities indicated above.

Examples of individual compounds in accordance with formula I are provided in the Examples section appended hereto. Compounds of formula I may be prepared as described in WO 03/018543 and WO 2004/013090. Specific examples are included herein. Preferred examples include cis-4-[(4-chlorophenyl)sulfonyl]-4-(2,5-difluorophenyl)cyclohexanepropanoic acid and the sodium salt thereof, which may prepared as described in WO 2004/013090.

Compounds in accordance with formula I have been shown to inhibit the proteolytic action of gamma-secretase towards a number of protein substrates, including Notch and APP, both in vitro and in vivo. Surprisingly, in vivo inhibition of gamma-secretase is obtained in the absence of the GI toxicity seen previously. Thus, representative compounds of formula I have been administered to several species (including man) over extended periods at doses sufficient to cause significant attenuation of gamma-secretase activity (evidenced by a reduction of plasma levels of Aβ, a product of the cleavage of APP by gamma secretase), without any evidence of GI toxicity.

In view of this desirable and unexpected activity profile, the compounds are suitable for use in treatment of conditions associated with Notch signalling, in particular cancer.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, lung, brain, testicular, stomach, pancreas, skin, small intestine, large intestine, throat, head and neck, oral, bone, liver, bladder, kidney, thyroid and blood.

Cancers that may be treated by the compounds, compositions and methods of the invention in particular include all types in which Notch signalling is known to play a role in the initial formation, proliferation or metastasis of cancerous cells. Modified Notch1 signalling has been implicated in lymphoblastic leukemia/lymphomas, mammary gland tumors, lung cancer, neuroblastomas, skin cancer, cervical cancer, epithelial tumors and prostate cancer. (Allenspach et. al., *Cancer Biology and Therapy,* 1:5, 466-476, 2002). Therefore compounds of the instant invention are useful in the treatment of the above described cancers.

Activating mutations in Notch1 are implicated in human T Cell Acute Lymphoblastic Leukemia (T-ALL) (Weng, et al., *Science,* 306:269-271 (2004)). Compounds of the instant invention are therefore useful in the treatment of T-ALL.

Cancers that may be treated by the compounds, compositions and methods of the invention include: breast, prostate, colon, ovarian, colorectal, brain and lung.

Cancers that may be treated by the compounds, compositions and methods of the invention include: lymphoma and leukemia.

Cancers that may be treated by the compounds, compositions and methods of the invention include breast cancer.

Cancers that may be treated by the compounds, compositions and methods of the invention include lung cancer, in particular non-small cell lung cancer. Cancers that may be treated by the compounds, compositions and methods of the invention include colon cancer and colorectal cancer.

Cancers that may be treated by the compounds, compositions and methods of the invention include brain cancer, including glioma, medulloblastoma and ependymoma.

Cancers that may be treated by the compounds, compositions and methods of the invention include familial adenomatous polyposis (FAP).

Cancers that may be treated by the compounds, compositions and methods of the invention include Barrett's esophagus.

Exposure to compounds of the instant invention has been shown to cause cell cycle arrest, in particular $G_0/G_1$ arrest, in populations of cells with a high level of Notch expression, but not in populations lacking such expression. Furthermore, it has been found that the arrested cells selectively undergo apoptosis. Hence, the compounds of the instant invention have the potential to selectively target malignant cells without damaging neighbouring healthy cells.

The compounds of the instant invention are suitable for treating cancer via the selective targeting of cancer stem cells.

The compounds of formula I may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds for the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

In a further example of intermittent dosing, the compounds of the instant invention are administered on three consecutive days followed by four days of rest.

In a yet further example of intermittent dosing, the compounds of the instant invention are administered on one day, followed by six days of rest.

In a yet further example of intermittent dosing, the compounds of the instant invention are administered on one day, followed by 10 to 13 days of rest.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidiny)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in WO 03/13526.

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta 3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl]methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ(i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthalmol.* 2001; 119: 709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid WO 01/60807, and 2(R)-7-(3-(2-chloro-4-(4-fluorophenoxy)phenoxy)propoxy)-2-ethylchromane-2-carboxylic acid WO 02/026729.

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p 53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, $5HT_3$ receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a $5HT_3$ receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is: 2-(R)-(1-(R)-(3,5-bis(trifluoromethyl)phenyl) ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfmavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with other γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with one or more of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepeside); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®);

gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimide); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofring); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/1-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, a γ-secretase and/or NOTCH inhibitor, an agent that interferes with receptor tyrosine kinases (RTKs), an agent that interferes with a cell cycle checkpoint, and any of the therapeutic agents listed above.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, a γ-secretase and/or NOTCH inhibitor, an agent that interferes with receptor tyrosine kinases (RTKs), an agent that interferes with a cell cycle checkpoint, and any of the therapeutic agents listed above.

Yet another embodiment of the invention is a method of treating cancer that comprises administering to a patient in need thereof a therapeutically effective amount of a compound of formula I or a pharmaceutically acceptable salt thereof in combination with a second medicament selected from: paclitaxel (Taxol®, optionally in combination with carboplatin); docetaxel (Taxotere®); trastuzumab (Herceptin®); tamoxifen (Nolvadex®); bevacuzimab (Avastin®); and erlotinib (Tarceva®).

The invention further encompasses a method of treating or preventing cancer that comprises administering to a patient in need thereof a therapeutically effective amount of a compound of formula I or a pharmaceutically acceptable salt thereof in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, a γ-secretase and/or NOTCH inhibitor, an agent that interfere with receptor tyrosine kinases (RTKs), an agent that interferes with a cell cycle checkpoint, and any of the therapeutic agents listed above.

Any of the specific dosages and dosage schedules applicable to the compounds of the instant invention may also be applicable to the therapeutic agents to be used in a combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally or intravenously. However, it is also within the scope of the present invention to administer a compound of the instant invention by one mode of administration, e.g. orally, and to administer the second therapeutic agent by another mode of administration, e.g. intravenously or by any of the other administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering") in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating cancer" and "treatment of cancer" encompass prophylactic treatments as well as treatments targeting an existing cancerous condition. Thus, the compounds of the instant invention may be administered to a patient alone or in combination with one or more conventional chemotherapeutic, radiotherapeutic or surgical interventions, for the purpose of arresting or attenuating an existing malignant condition by killing cancerous cells. However, said compounds may also be administered simultaneously with or subsequent to a conventional chemotherapeutic, radiotherapeutic or surgical intervention for the purpose of preventing or delaying the recurrence or metastasis of cancerous cells.

All patents, publications and pending patent applications identified are hereby incorporated by reference.

Suitable methods of assaying the level of activity of compounds of the present invention towards γ-secretase are disclosed in WO 01/70677, WO 03/093252, and in *Biochemistry,* 2000, 39(30), 8698-8704 (APP as substrate); and in *Biochemistry* (2003), 42, 7580-7586 (Notch as substrate).

The Examples of the present invention all had an $ED_{50}$ of less than 1 μM, typically less than 0.1 μM and in preferred cases less than 10 nM in the above-referenced assays.

The following examples illustrate the present invention.

Assay for Cell Cycle Arrest Cells expressing Notch (ALL-SIL, DND-41, HPB-ALL or TALL-1) (Weng et al, *Science,* 306 (2004), 269-71) were incubated in the presence or absence of a compound of the instant invention (e.g. the compound of Example 39 below) at concentrations up to 10 μM. At the end of the incubation (typically 4-8 days), the cells were collected, fixed in 70% ethanol on ice for >2 hours, washed, then labelled for 15 min at 37° C. with propidium iodide (0.2 mg/ml) (PI) in the presence of 0.1% Triton X100 and 0.2 mg/ml RNase and subjected to FACS analysis. In comparison to untreated controls, treated cell cultures showed severe loss of $G_2$- and S-phase populations, consistent with $G_0/G_1$ arrest.

Assay for Apoptosis

This assay relies on the detection of phosphatidylserine (PS) on the external surface of apoptotic cells via binding to Annexin V, since PS in intact cells remains inaccessible. The bound Annexin V is labelled with FITC-conjugated antibody for analysis by FACS. Kits for carrying out this assay are available commercially (e.g. from BD cat. no. 556547).

Cells were incubated as described above in the presence of Annexin V, then collected, washed, labelled with FITC-Annexin V and PI antibodies, and analysed by FACS. Due to exposure of PS-bound Annexin V on the outside of apoptotic, but not normal, cells, FACS technologies enables quantification of the population of apoptotic cells highly stained by FITC-conjugated antibodies raised against Annexin V.

Typically, cells treated with 0.1% DMSO for 7 days showed negligible accessible expression of Annexin V, the bulk of the cell population remaining unstained. In contrast, exposure to compounds of the instant invention at 10 μM for 7 days (replenished twice during the experiment) lead to a reduction of the number of such cells with low accessibility of Annexin V, and the appearance of a highly labelled population of cells, consistent with known redistribution of this protein during apoptosis. Subsequent experiments failed to show equivalent apoptosis when the duration of treatment (4 days) was insufficient to cause cell cycle arrest, or the concentration of inhibitor was insufficient to cause arrest, or when a Notch-independent cell line was used. Furthermore, a titration comparison of representative inhibitors in HPB-ALL cells over 6 days revealed a perfect correlation between the treatments that caused apoptosis and those that caused parallel cell cycle arrest.

Assay for Cell Viability

Cell lines such as ALL-SIL, DND-41, HPB-ALL, and T-ALL-1 cell lines were seeded to 96 well plates ($1 \times 10^4$ cells in 90 μl/well) in media specified by the cell line supplier (DSMZ, German National Resource Centre for Biological Material). Following overnight incubation of 90 μl at 37° C. in 5% $CO_2$, 10 μl of media containing 10×γ-secretase inhibitor stock was added, yielding a final concentration of 0.1% DMSO. Media containing inhibitor (75 μl) was replaced after a brief centrifugation every 2 days and the cells were completely resuspended. Cell viability was measured following 8 days of treatment using ATPlite (PerkinElmer), according to the manufacturer's instructions.

Assay to Measure Gamma-Secretase Inhibition by Monitoring Cleavage of the Substrate Notch 1

Treated cells were lysed in buffer containing 1% Triton X-100, 0.5% NP-40, 0.2% SDS in TBS and vortexed. Samples were rocked for 25 minutes at 4° C., sonicated for 15 seconds and centrifuged at 14,000 xg to collect supernatant. Protein was quantitated using the Biorad DC Protein assay (#500-0116) and 30-50 µg of protein separated on 10-20% Tricine gel. Proteins were transferred to nitrocellulose membranes, blocked in 10% Milk for 1 hour, and probed with cleaved Notch 1 antibody (#2421, Cell Signaling Technologies) diluted 1:1000 in PBS overnight at 4° C. Membranes washed in PBS were subsequently probed with anti-rabbit-HRP at 1:7000 for 1 h and proteins revealed to film using Pierce SuperSignal West Femto.

Assay to Measure Inhibition of the Notch Pathway by Monitoring Notch Target Genes Response in Cells or Tumors RNA was extracted according to the RNeasy kit from Qiagen and cDNA prepared as described by Applied Biosystems using the High Capacity cDNA Archive kit. Notch pathway response genes such as Hes1 and Hes5 were quantitated using Taqman Real-Time PCR with probes purchased from Applied Biosystems.

Assay for Anti-Tumor Activity

CD1 nude mice predosed with cyclophosphamide (100 mg/kg, i.p. for 3 days) were injected subcutaneously with $5\times10^6$ T-ALL-1 cells per mouse in PBS/matrigel. Tumor volume was monitored with calipers and when this reached ~250 mm$^3$ the mice were dosed orally 4 days-On, 4-days-Off for a period of 24-32 days using inhibitor formulated in 0.5% methylcellulose. Body weight and tumor volume were recorded daily and all procedures were conducted according to IACUC guidelines.

EXAMPLES

Intermediate 1

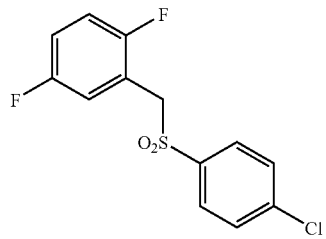 [SMILES: O=S(=O)(Cc1cc(F)ccc1F)c1ccc(Cl)cc1]

4-Chlorothiophenol (3.6 g, 0.025 mol) in dichloromethane (100 ml) was treated with 2,5-difluorobenzyl bromide (5.17 g, 0.025 mol) and triethylamine (3.9 ml, 0.028 mol), reaction was stirred for 2 hours then diluted with dichloromethane (250 ml) and washed with water (100 ml) and brine (100 ml). The separated organic layer was dried (MgSO$_4$) and evaporated to dryness. Product was purified by passing down a plug of silica eluting with hexane-ethyl acetate mixtures. 5.12 g. $^1$H NMR CDCl$_3$ 7.23 (4H, s), 6.69-6.86 (3H, m) and 4.04 (2H, s).

This thioether (5.12 g, 0.018 mol) was dissolved in dichloromethane (100 ml) and treated with m-chloroperoxybenzoic acid (14.3 g, 0.042 mol (50% w/w)) and stirred for 2 hours. The reaction was then washed with Na$_2$S$_2$O$_5$ (5% solution, 100 ml), brine (50 ml), dried (MgSO$_4$) and evaporated to dryness. The sulphone product was purified on silica eluting with hexane-ethyl acetate mixtures, 3.6 g. $^1$H NMR CDCl$_3$ 7.61 (2H, d, J=8.6 Hz), 7.45 (2H, d, J=8.6 Hz), 7.13-7.08 (1H, m), 7.05-7.01 (1H, m), 7.05-7.00 (1H, m), 6.99-6.87 (1H, m) and 4.36 (2 h, s).

Intermediate 2

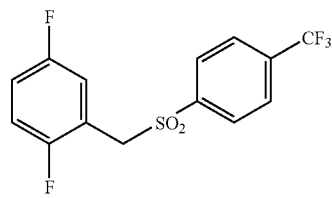

Prepared as for Intermediate 1, using 4-trifluoromethylthiophenol, and obtained as a solid. $^1$H NMR (360 MHz, CDCl$_3$) δ 7.85-7.83 (2H, m), 7.76-7.74 (2H, m), 7.15-7.10 (1H, m), 7.06-7.0 (1H, m), 6.92-6.86 (1H, m) and 4.46 (2H, s).

Preparation 1

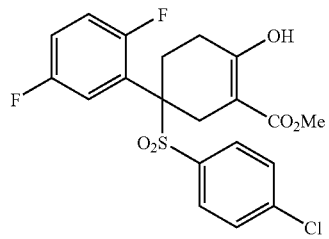 [SMILES: COC(=O)C1=C(O)CCC(c2cc(F)ccc2F)(S(=O)(=O)c2ccc(Cl)cc2)C1]

Intermediate 1 (1 g, 3.3 µmol) and methyl acrylate (0.84 ml, 9.27 mmol) in tetrahydrofuran (30 ml) were treated dropwise with potassium $^t$butoxide (3.64 ml µM solution in tetrahydrofuran, 3.64 mmol). The reaction was stirred for 2 hours, diluted with ethyl acetate (100 ml) and washed with water (50 ml) and brine (50 ml). The organic phase was separated, dried (MgSO$_4$) and evaporated to dryness, and the product purified on silica eluting with hexane-ethyl acetate mixtures. (1.0 g). $^1$H NMR CDCl$_3$ 12.0 (1H, s), 7.41 (4H, s), 7.06-7.0 (2H, m), 6.87-6.81 (1H, s), 3.81 (3H, s), 3.38 (1H, dd, J=3.2, 15.8 Hz), 3.02-2.92 (2H, m), 2.52 (1H, dd, J=5.7, 18.5 Hz), 2.3-2.2 (1H, m) and 2.2-2.1 (1H, m).

Preparation 2

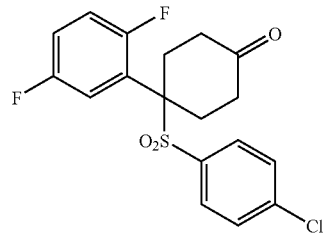 [SMILES: O=C1CCC(c2cc(F)ccc2F)(S(=O)(=O)c2ccc(Cl)cc2)CC1]

The ester from Preparation1 (1.0 g, 2.25 mmol) in dimethylsulfoxide (10 ml) was treated with NaCl (0.3 g, 4.96 mmol)

and water (0.9 ml, 4.96 mmol) and heated at 150° C. for 2 hours. The cooled reaction mixture was diluted with ethyl acetate (100 ml), washed with saturated NH₄Cl (100 ml), and the organic phase separated, dried (MgSO₄) and evaporated to dryness. The product was purified on silica eluting with hexane-ethyl acetate mixtures, 0.5 g. ¹H NMR CDCl₃ 7.43-7.37 (4H, m), 7.22-7.1 (2H, m), 6.97-6.9 (1H, m), 3.05-2.98 (2H, m) and 2.61-2.53 (2H, m).

Preparation 3

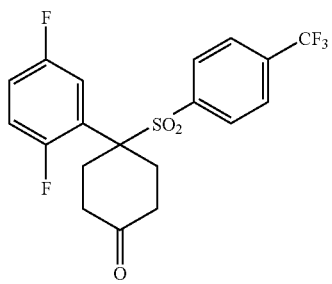

Prepared by the procedures of Preparations 1 and 2 using Intermediate 2 to give the product as a solid. (0.3 g) ¹H NMR (360 MHz, CDCl₃) δ 7.71-7.69 (2H, d, J=7.5 Hz), 6.62-6.60 (2H, d, J=7.4 Hz), 7.22-7.11 (2H, m), 6.95-6.88 (1H, m), 3.02-2.99 (2H, m), 2.63-2.54 (4H, m) and 2.25-2.16 (2H, m).

Preparation 4

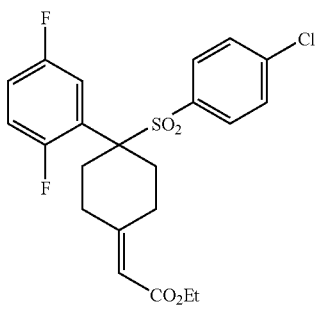

Ethyl (diethoxyphosphinyl)acetate (5.16 mL, 26 mmol) was added dropwise to a slurry of sodium hydride (60% dispersion in mineral oil, 988 mg, 24.7 mmol) in tetrahydrofuran (60 mL) and the mixture was stirred at room temperature for 1 h. The ketone from Preparation 2 (5 g, 13 mmol) in tetrahydrofuran (50 mL) was added dropwise over 20 min. and the mixture was stirred at room temperature for 18 h. Water was added and the mixture was extracted with ethyl acetate. The combined organic fractions were washed with water, dried (MgSO₄) and the solvent was evaporated under reduced pressure. The residue was purified by flash column chromatography on silica gel, eluting with isohexane:EtOAc (85:15), to give the product as a white solid (5.2 g, 88%). ¹H NMR (400 MHz, CDCl₃) δ 7.41-7.36 (4H, m), 7.18-7.13 (1H, m), 7.11-7.05 (1H, m), 6.93-6.86 (1H, m), 5.64 (1H, s), 4.14-4.10 (2H, m), 3.99-3.96 (1H, m), 2.91-2.80 (2H, m), 2.42-2.38 (1H, m), 2.31-2.04 (3H, m), 1.89-1.78 (1H, m), 1.28-1.24 (3H, m).

Preparation 5

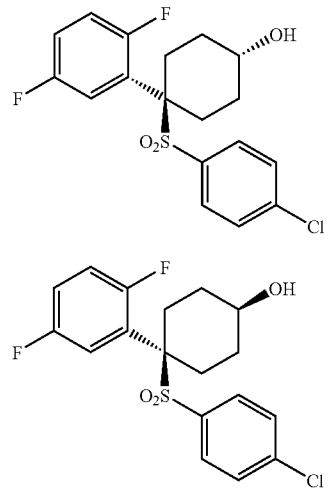

The ketone from Preparation 2, (0.1 g, 0.26 mmol) in methanol (2 ml) was treated with NaBH₄ (0.098 g, 0.26 mmol) and stirred for 1 hour. The reaction was quenched with HCl (1N, 10 ml), diluted with ethyl acetate (20 ml), then the organic phase was separated, dried (MgSO₄) and evaporated to dryness. The cis and trans products were purified on silica eluting with hexane-ethyl acetate mixtures.

(a) (trans) 0.052 g. ¹H NMR CDCl₃ 7.39-7.33 (4H, m), 7.11-7.02 (2H, m), 6.88-6.82 (1H, m), 3.80-3.73 (1H, m), 2.80-2.60 (2H, m), 2.22-2.16 (2H, m), 2.08-2.04 (2H, m), 1.53 (1H, br) and 1.27-1.13 (2H, m).

(b) (cis) ¹H NMR (CDCl₃) 7.40 (4H, s), 7.16-7.03 (2H, m), 6.90-6.83 (1H, m), 3.97-3.95 (1H, m), 3.77-3.68 (1H, m), 3.51-3.49 (1H, m), 2.61-2.53 (2H, m), 1.91-1.83 (2H, m) and 1.50-1.42 (2H, m).

Preparation 6

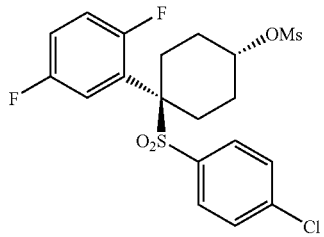 [SMILES: CS(=O)(=O)O[C@H]1CC[C@](c2cc(F)ccc2F)(S(=O)(=O)c2ccc(Cl)cc2)CC1]

The trans cyclohexanol from Preparation 5 (2.7 g, 6.9 mmol) and triethylamine (1.45 mL, 10.3 mmol) in dichloromethane (50 mL) were treated with methane sulphonyl chloride (0.645 mL, 8.9 mmol) at −30° C. After 30 mins the mixture was washed with water (20 mL), 10% aqueous citric acid (20 mL) and saturated aqueous sodium hydrogen carbonate (50 mL), dried (MgSO₄) and evaporated to dryness. The solid was triturated with ether to give the mesylate (2.6 g)

¹H NMR (CDCl₃) 7.40-7.37 (4H, m), 7.12-7.07 (2H, m), 6.92-6.83 (1H, m), 4.78-4.65 (1H, m), 2.96 (3H, s), 2.88-2.52 (2H, m), 2.29-2.21 (4H, m) and 1.59-1.47 (2H, m).

Preparation 7

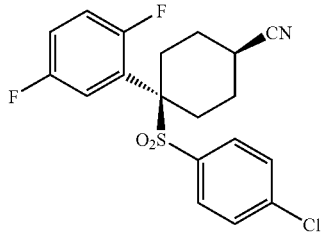 [SMILES: N#C[C@H]1CC[C@@](c2cc(F)ccc2F)(S(=O)(=O)c2ccc(Cl)cc2)CC1]

The trans mesylate from Preparation 6 (103 mg, 0.22 mmol) was dissolved in toluene (20 ml) and added to a preazeotroped sample of tetrabutylammonium cyanide (354 mg, 1.32 mmol). and the mixture was warmed to 70° C. over 18 hr and then cooled to rt. The solution was diluted with water (10 ml) and washed with ethyl acetate (2×50 ml). The organic phase was washed with brine (10 ml), dried (MgSO₄) and evaporated. The clear oil obtained was purified by column chromatography on silica gel eluting with 10-20% ethyl acetate in hexanes, to give the cyanide. ¹H NMR (CDCl₃) 7.42-7.36 (4H, s), 7.10-7.05 (2H, m), 6.89-6.84 (1H, m), 2.88-2.86 (1H, m), 2.76-2.72 (2H, m), 2.52-2.45 (1H, m), 2.12-2.07 (1H, m) and 1.56-1.49 (1H, m).

Preparation 8

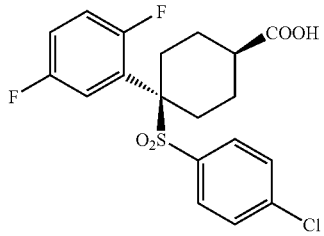 [SMILES: O=C(O)[C@H]1CC[C@@](c2cc(F)ccc2F)(S(=O)(=O)c2ccc(Cl)cc2)CC1]

The cyanide from Preparation 7 (143 mg, 0.36 mmol) was dissolved/suspended in a mixture of glacial acetic acid (10 ml) and conc. HCl (6 ml) and heated at 110° C. for 15 hours. The mixture was cooled, diluted with ethyl acetate and washed with water (x3), dried (MgSO₄) and evaporated to dryness. This crude residue (153 mg) was purified by preparative tlc (5% methanol in dichloromethane/1% acetic acid). ¹H NMR (CDCl₃) 7.38-7.35 (4H, s), 7.08-7.06 (2H, m), 6.90-6.84 (1H, m), 2.65-2.58 (2H, m), 2.38-2.33 (3H, m), and 1.75-1.49 (4H, m).

Preparation 9

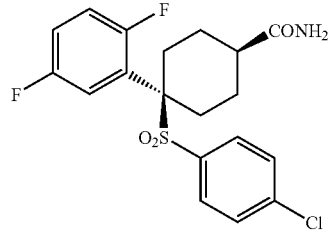 [SMILES: NC(=O)[C@H]1CC[C@@](c2cc(F)ccc2F)(S(=O)(=O)c2ccc(Cl)cc2)CC1]

The cyanide from Preparation 8 (50 mg, 0.12 mmol) was dissolved in a mixture of tetrahydrofuran (4.5 ml) and water (0.5 ml) and stirred at 20° C. The mixture was treated with hydrogen peroxide (20 ml, 0.6 mmol) and then with lithium hydroxide (6 mg, 0.25 mmol) for 2 hours. Hydrogen peroxide (20 ml, 0.6 mmol) and then with lithium hydroxide (6 mg, 0.25 mmol) were added and the mixture was stirred at rt. for 72 hrs. The mixture was cooled, diluted with ethyl acetate and washed with water (x2) and sat. sodium bisulphite, dried (MgSO₄) and evaporated to dryness. This crude residue (51 mg) was purified by preparative tlc (20% ethyl acetate in hexanes) ¹H NMR (CDCl₃) 7.37 (4H, s), 7.10-7.02 (2H, m), 6.90-6.84 (1H, m), 5.57 (2H, brs), 2.54-2.48 (3H, m), 2.43-2.39 (1H, m), 2.19-2.15 (2H, m) and 1.62-1.50 (3H, m).

Example 1

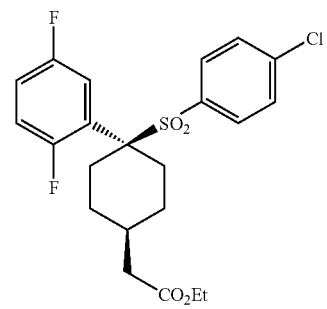

Sodium borohydride (313 mg, 8.23 mmol) was added to a mixture of the unsaturated ester from Preparation 4 (3.74 g, 8.23 mmol) and nickel (II) chloride (2.67 g, 20.6 mmol) in ethanol (100 mL). The mixture was stirred at room temperature for 20 min., then water (100 mL) was added. The mixture was filtered through Hyflo™, washing with ethanol and ethyl acetate. The solvent was evaporated under reduced pressure and the residue was partitioned between ethyl acetate and water. The organic layer was collected, dried (MgSO₄) and the solvent was evaporated under reduced pressure. The residue was purified by flash column chromatography on silica gel, eluting with isohexane:EtOAc (85:15), to give the faster running cis-isomer, as an oil (1.36 g, 36%), ¹H NMR (400 MHz, CDCl₃) δ 7.37-7.30 (4H, m), 7.09-7.00 (2H, m), 6.86-6.79 (1H, m), 4.14 (2H, q, J=7.1 Hz), 2.47 (2H, d, J=7.6 Hz), 2.46-2.38 (2H, m), 2.19-2.14 (1H, m), 1.76-1.71 (2H, m), 1.57-1.48 (4H, m), 1.27 (3H, t, J 7.1 Hz);

and also the slower running trans-isomer, as an oil (200 mg, 5.3%).

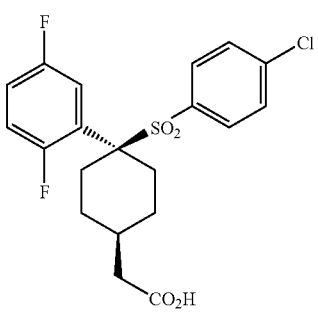

Example 2

Lithium hydroxide (350 mg, 14.57 mmol) was added to a solution of the cis-ester from Example 1, (1.33 g, 2.91 mmol) in ethanol (40 mL). The mixture was degassed and stirred at room temperature under nitrogen gas for 5 h. The mixture was poured into aqueous hydrochloric acid (1M) and extracted with ethyl acetate. The organic extract was dried (MgSO$_4$) and the solvent was evaporated under reduced pressure to give a white solid which was then crystallized from IPA to give the product as a white solid (950 mg, 76%). $^1$H NMR (400 MHz, CD$_3$OD) δ 7.51-7.49 (2H, m), 7.40-7.37 (2H, m), 7.19-7.10 (2H, m), 7.00-6.94 (1H, m), 2.51-2.35 (6H, m), 2.13-2.10 (1H, m), 1.78-1.74 (2H, m), 1.57-1.50 (2H, m).

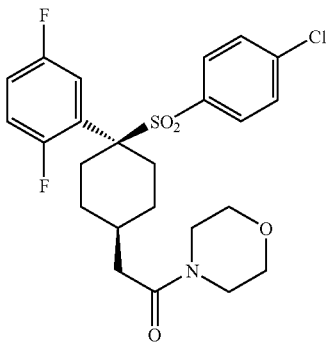

Example 3

The acid from Example 2 (50 mg, 0.117 mmol), morpholine (30 μL, 0.351 mmol), 1-hydroxybenzotriazole (24 mg, 0.176 mmol) and triethylamine (65 μL, 0.468 mmol) was stirred in tetrahydrofuran at room temperature under nitrogen gas for 10 min 1-(3-Dimethylaminopropyl)-3-ethylcarbodiimide hydrochloride (45 mg, 0.234 mmol) was added to the mixture and stirred for 24 h. The mixture was poured into aqueous sodium hydroxide (1M) and extracted with ethyl acetate. The organic extract was dried (MgSO$_4$) and the solvent was evaporated under reduced pressure. The residue was purified by flash column chromatography on silica gel, eluting with 5 to 10% methanol in dichloromethane, to give the product as a white foam (50 mg, 86%). $^1$H NMR (400 MHz, CD$_3$OD) δ 7.50 (2H, d, J 8.6 Hz), 7.37 (2H, d, J 8.6 Hz), 7.19-7.09 (2H, m), 7.00-6.93 (1H, m), 3.69-3.63 (4H, m), 3.59-3.56 (4H, m), 2.55 (2H, d, J 7.4 Hz), 2.47-2.39 (4H, m), 2.16-2.07 (1H, m), 1.78-1.74 (2H, m), 1.58-1.51 (2H, m). m/z (ES$^+$) (M+1) 498+500.

Examples 4-15

The following compounds were prepared according to the method of Example 3, using the appropriate amine in place of morpholine.

| Ex. | NR$_2$ | Formula | M.W. | m/z (ES$^+$) (M + 1) |
|---|---|---|---|---|
| 4 | —N(CH$_2$CH$_2$)$_2$N—CH$_3$ (piperazine-N-methyl) | C$_{25}$H$_{29}$ClF$_2$N$_2$O$_3$S | 510, 512 | 511, 512 |
| 5 | —N(CH$_2$CH$_2$)$_2$N—Ph | C$_{30}$H$_{31}$ClF$_2$N$_2$O$_3$S | 572, 574 | 573, 575 |
| 6 | —N(piperidine)—OH | C$_{25}$H$_{28}$ClF$_2$NO$_4$S | 511, 513 | 512, 514 |
| 7 | —NH—CH$_2$-(2-pyridyl) | C$_{27}$H$_{27}$ClF$_2$N$_2$O$_3$S | 532, 534 | 533, 535 |
| 8 | —NH—(CH$_2$)$_3$-imidazolyl | C$_{26}$H$_{28}$ClF$_2$N$_3$O$_3$S | 535, 537 | 536, 538 |
| 9 | —N(piperidine)—CO$_2$Et (4-) | C$_{28}$H$_{32}$ClF$_2$NO$_5$S | 567, 569 | 568, 570 |
| 10 | —N(piperidine)—CO$_2$Et (3-) | C$_{28}$H$_{32}$ClF$_2$NO$_5$S | 567, 569 | 568, 570 |
| 11 | —N(piperidine)—CO$_2$Et (3-, stereo) | C$_{28}$H$_{32}$ClF$_2$NO$_5$S | 567, 569 | 568, 570 |

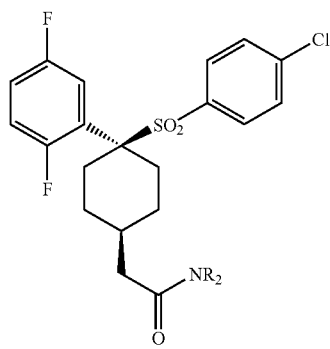

| Ex. | NR₂ | Formula | M.W. | m/z (ES⁺) (M + 1) |
|---|---|---|---|---|
| 12 | —N(piperidine-3-CO₂Et) | C₂₈H₃₂ClF₂NO₅S | 567 569 | 568 570 |
| 13 | —N(piperidine) | C₂₅H₂₈ClF₂NO₃S | 495 497 | 496 498 |
| 14 | —N(piperidine-3-Me-3-CO₂Et) | C₂₉H₃₄ClF₂NO₅S | 581 583 | 582 584 |
| 15 | —N(piperidine-3-Me-3-CO₂Et) | C₂₉H₃₄ClF₂NO₅S | 581 583 | 582 584 |

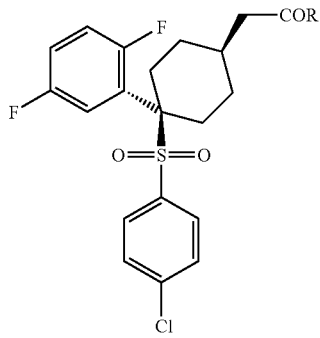

Examples 16-33

These Examples were prepared by the following method, using the appropriate amine free base or amine salt with prior neutralization.

To a stirred suspension of cis 4-(4-chlorobenzenesulphonyl)-4-(2,5-difluorophenyl)cyclohexaneacetic acid (Example 2, 0.15 g, 0.35 mmol) in dichloromethane (5 ml) was added oxalyl chloride (0.05 ml, 0.57 mmol) and dimethylformamide (1 drop). After 30 minutes the solution was evaporated to a small volume and to a solution of the residue in dichloromethane (5 ml) was added the desired amine (1.75 mmol). After stirring the solution for 20 minutes the solvent was removed in vacuo and the residue purified by chromatography on silica gel eluting with increasing concentrations of ethyl acetate in isohexane (25%, 50%). The fractions containing the product were evaporated to give the product amide. Chromatographic purification was performed on silica gel using appropriate concentrations of ethyl acetate in isohexane, ethyl acetate or methanol in ethyl acetate where appropriate.

| Example No. | R | MS m/z (M + H) | m.p. |
|---|---|---|---|
| 16 | NH-cyclobutyl | 482,484 | 192-193° C. |
| 17 | NH₂ | 428,430 | 187-189° C. |
| 18 | NHMe | 442,444 | 200-201° C. |
| 19 | NHEt | 456,458 | 146-147° C. |
| 20 | NHⁿPr | 470,472 | 150-151° C. |
| 21 | NHⁱPr | 470,472 | 124-125° C. |
| 22 | NMe₂ | 456,458 | |
| 23 | NHCH₂CH₂Ph | 532,534 | |
| 24 | NHCH₂CF₃ | 510,512 | |
| 25 | N(thiomorpholine-1,1-dioxide) | 546,548 | |
| 26 | NHCH₂-cyclopropyl | 482,484 | 187-188° C. |
| 27 | NH-cyclopentyl | 496,498 | 182-183° C. |
| 28 | NH-cyclopropyl | 468,470 | 145-147° C. |
| 29 | NHⁿBu | 484,486 | oil |
| 30 | NHⁱBu | 484,486 | 102-110° C. |
| 31 | NHCH(Et)₂ | 498,500 | 89-92° C. |
| 32 | NH-allyl | 468,470 | 132-134° C. |

Example 33

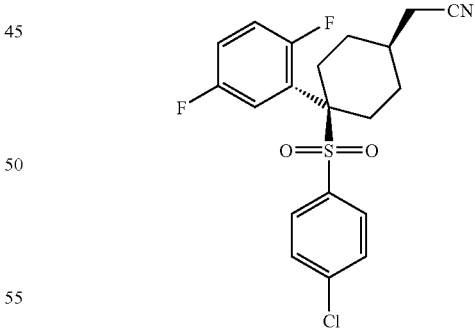

To a solution of the cis amide from Preparation 9 (46 mg) and pyridine (0.053 ml) in tetrahydrofuran (1 ml) was added trifluoroacetic anhydride (0.056 ml). The solution was stirred at room temperature for 2 hours when 0.5M-HCl (aqueous) and ethyl acetate were added. The organic phase was dried (MgSO₄), evaporated to a small volume and purified by chromatography on silica gel, eluting with isohexane:ethyl acetate (5:1) to give the desired product as a colourless solid. ¹H NMR (360 MHz, CDCl₃) Λ1.61-1.70 (2H, m), 1.86-1.94 (2H, m), 2.03-2.10 (1H, m), 2.42-2.45 (4H, m), 2.51 (2H, d J 8.0 Hz), 6.8 (1H, m), 7.02-7.09 (2H, m), 7.30 (2H, d J 8.6 Hz), 7.36 (2H, d J 8.7 Hz).

Example 34

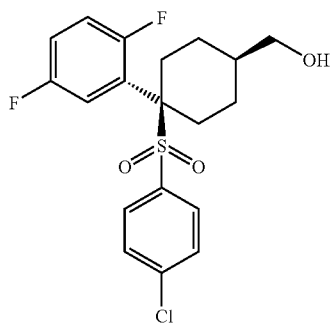

The acid from Preparation 8 (153 mg) was dissolved in dry THF (10 ml) and cooled to 0° C. under nitrogen. Triethylamine (61 μL, 0.43 mmol) and isobutylchloroformate (57 μL, 0.43 mmol) were added and the mixture stirred at 0° C. for one hour. The precipitate that had formed was removed by filtration and washed with a further 5 ml of dry THF. The combined THF layers were recooled to 0° C. and sodium borohydride (70 mg, 1.84 mmol) as a solution in water (2 ml) was added with effervescence. After stirring for 30 minutes at 0° C., the reaction was diluted with ethyl acetate, washed with ammonium chloride solution, sodium bicarbonate solution and brine then dried (MgSO$_4$) and evaporated to dryness. The residue was purified by column chromatography eluting with ethyl acetate:hexane (1:3) to afford the desired alcohol (75 mg). $^1$H NMR (CDCl$_3$) 7.39-7.31 (4H, m), 7.10-7.01 (2H, m), 6.88-6.81 (1H, m), 3.71 (2H, d, J=7.5 Hz), 2.46-2.32 (4H, m), 1.90-1.85 (2H, m), 1.78-1.74 (1H, m) and 1.54-1.44 (2H, m). m/z=423 [MNa]$^+$ Example 35

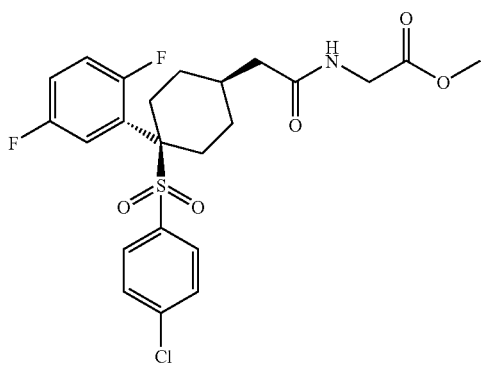

Step (1)

To a solution of the acid from Example 2 (1 g) in DCM (50 ml) and ethyl acetate (30 ml) was added pentafluorophenol (1.5 equiv.) and DCC (1.5 equiv.) and stirred at room temperature for 1 h. The reaction mixture was evaporated in vacuo, taken up in ethyl acetate and filtered. The filtrate was evaporated in vacuo to yield the pentafluorophenol ester of sufficient purity to use in subsequent reactions.

Step (2)

To the pentafluorophenol ester prepared in Step (1) (155 mg, 0.25 mmol) dissolved in DMF (3 ml) and under nitrogen were added glycine methyl ester hydrochloride (125 mg, 1.0 mmol) and triethylamine (0.15 ml). After 2 h the reaction was diluted with water, extracted with ethyl acetate (x3), washed with, water, brine, dried (MgSO$_4$), filtered and evaporated. Purified by flash column chromatography (1:1 $^i$hexane/ethyl acetate to 9:1 ethyl acetate/methanol) to give a white solid (55 mg). $^1$H-NMR (CDCl$_3$) 1.08-1.16 (1H, m), 1.30-1.37 (1H, m), 1.67-1.71 (1H, m), 1.75-1.79 (2H, m), 1.91-1.95 (1H, m), 2.20-2.26 (1H, m), 2.41 (4H, d, J=7.8 Hz), 3.77 (3H, s), 4.05 (2H, d, J=5.1 Hz), 6.19 (1H, br), 6.79-6.85 (1H, m), 7.00-7.07 (2H, m), 7.30-7.37 (4H, m).

Example 36

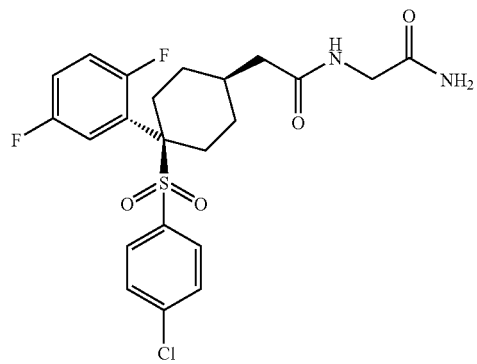

The glycine ester prepared in Example 35 (50 mg, 0.1 mmol) in a sealed tube and dissolved in a 2M ammonia in methanol solution (3 ml) was heated to 50° C. for 3 h. After cooling to room temperature the reaction mixture was concentrated and purified by trituration with ether to give a white solid (28 mg). MS (EI+): 485 (MH+)

Example 37

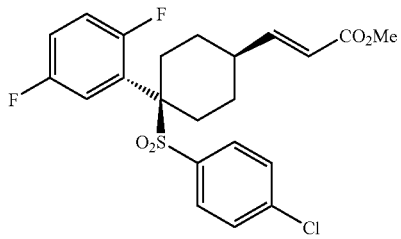

The alcohol from Example 34 (4 g, 10 mmol) was dissolved in dichloromethane (280 ml) and was treated with Dess Martin periodinane (4.66 g, 1 μmol) and the mixture was stirred for 45 mins before adding saturated aqueous sodium bisulphite (100 ml) and after 5 mins the mixture was separated and the organic phase as washed with saturated aqueous sodium bicarbonate (100 ml) dried (MgSO$_4$) and evaporated to dryness. The crude residue (4 g) was dissolved in dry dichloromethane (100 ml) and treated with methyl triphenylphosphinoacetate (4.7 g 14 mmol), stirring at rt. for 16 hrs. The solvent was evaporated and the residue was purified by column chromatography on silica gel eluting with 10-20% ethyl acetate in hexanes, to give the product. ¹H NMR (CDCl₃) 7.37-7.36 (4H, m), 7.10-7.02 (3H, m), 6.87-6.83 (1H, m), 5.91 (1H, d, J=16 Hz), 3.77 (3H, s), 2.55-2.45 (3H, m), 2.40-2.38 (2H, m), 1.95-1.90 (2H, m) and 1.65-1.52 (2H, m).

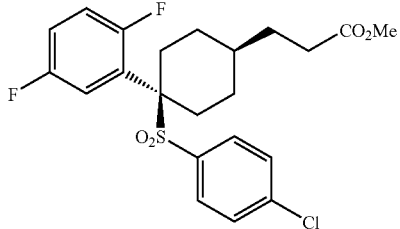 [SMILES: COC(=O)CC[C@H]1CC[C@@](c2cc(F)ccc2F)(S(=O)(=O)c2ccc(Cl)cc2)CC1]

Example 38

The alkene from Example 37 (3.6 g, 9 mmol) was dissolved in ethyl acetate (350 ml). The flask was degassed and then 10% palladium on carbon (400 mg) was added and the mixture stirred under an atmosphere of hydrogen for 45 mins. The solution was filtered through Celite™ and evaporated. The clear oil obtained was purified by preparative tlc eluting with 5% ethyl acetate in hexanes. The oil obtained was then further purified by column chromatography on silica gel eluting with 5-10% ethyl acetate in hexane to give the product. ¹H NMR (CDCl₃) 7.37-7.34 (4H, m), 7.08-7.00 (2H, m), 6.85-6.81 (1H, m), 3.67 (3H, s), 2.45-2.39 (4H, m), 2.33 (2H, t, J=8.4 Hz), 1.81 (2H, q, J=8.4 Hz), 1.72-1.68 (2H, m) and 1.60-1.43 (3H, m).

Example 39

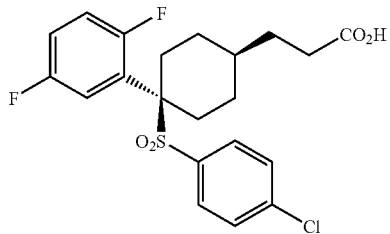 [SMILES: O=C(O)CC[C@H]1CC[C@@](c2cc(F)ccc2F)(S(=O)(=O)c2ccc(Cl)cc2)CC1]

The ester from Example 38 (104 mg, 0.23 mmol) was dissolved in a mixture of ethanol (10 ml) and water (3 ml) and stirred at 20° C. The flask was degassed and then lithium hydroxide (27 mg, 1.15 mmol) was added. The mixture was stirred for 3 hrs. at room temperature. 1N Hydrochloric acid was then added and the mixture was washed with ethyl acetate (2×50 ml). The organic phase was washed with brine (50 ml), dried (MgSO₄) and evaporated. The oil obtained was then further purified by preparative tlc eluting with ethyl acetate to give the acid. ¹H NMR (CDCl₃) 7.37-7.30 (4H, m), 7.09-6.99 (2H, m), 6.85-6.79 (1H, m), 2.42-2.36 (6H, m), 1.85-1.79 (2H, m), 1.73-1.69 (2H, m), 1.63-1.58 (1H, m) and 1.53-1.45 (2H, m).

Example 40

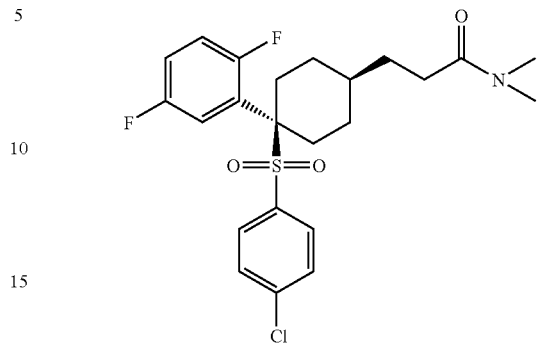

The acid from Example 39 (52 mg, 0.118 mmol) in dichloromethane (2 ml) was treated with oxalyl chloride (88 μl, 2 M solution in dichloromethane, 0.176 mmol). A drop of N,N-dimethylformamide was added and the solution allowed to stir for 2 hours. After this time, solvent was removed in vacuo and the residue redissolved in dichloromethane (1 ml). This solution was dripped into methanolic ammonia (2 M, 2 ml). The reaction was evaporated in vacuo and the residue chromatographed on silica, eluting with 80% ethyl acetate in hexanes. The resulting material was purified further by preparative t.l.c., eluting with 100% ethyl acetate followed by recrystallisation from hot hexane to give product (7.4 mg, 14%). ¹H NMR (360 MHz, CDCl₃), 1.45-1.53 (2H, m), 1.57-1.65 (1H, br), 1.70-1.75 (2H, m), 1.78-1.84 (2H, m), 2.32 (2H, t, J=15.3 Hz), 2.38-2.44 (4H, br), 2.95 (3H, s), 3.02 (3H, s), 6.79-6.86 (1H, m), 7.00-7.09 (2H, m), 7.31-7.37 (4H, m); ms. (ES⁺), 470 (M⁺1), 294 (M⁺175).

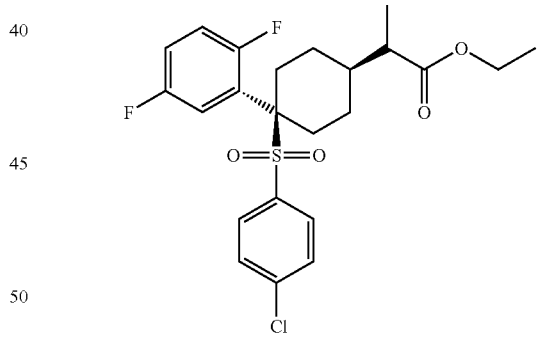

Example 41

The cis-ester from Example 1 (669 mg, 1.467 mmol) in tetrahydrofuran (14 ml) was cooled to −78° C., treated with sodium bis(trimethylsilyl)amide (2.20 ml, 1 M solution in tetrahydrofuran, 2.20 mmol) and stirred while warming to room temperature over 2 hours. Methyl iodide (457 μl, 7.36 mmol) was then added to the mixture at −20° C. and stirring continued, again warming to room temperature, for 2 hours. The reaction was quenched with glacial acetic acid (132 μl, 2.20 mmol), diluted with ammonium chloride (50% aq., 80 ml) and extracted with ethyl acetate (3×100 ml). Combined organics were then washed with brine (sat., 200 ml), dried (MgSO$_4$) and evaporated in vacuo to give crude (670 mg). This material was chromatographed on silica, eluting with 8% ethyl acetate in hexanes to give product (272 mg, 40%). $^1$H NMR (400 MHz, CDCl$_3$), 1.16 (3H, d, J=6.9 Hz), 1.28 (3H, t, J=7.1 Hz), 1.45-1.51 (2H, m), 1.71-1.77 (2H, m), 1.89-1.94 (1H, m), 2.28-2.48 (3H, br), 2.54-2.60 (1H, br), 2.70-2.74 (1H, m), 4.09-4.18 (2H, m), 6.77-6.84 (1H, m), 6.99-7.08 (2H, m), 7.26-7.36 (4H, m).

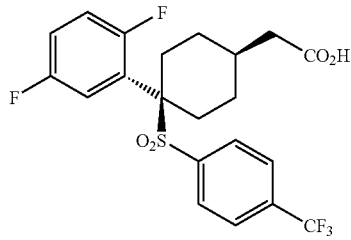

Example 42

Prepared from the ketone of Preparation 3, following the procedures of Preparation 4 and Examples 1 and 2. $^1$H NMR (360 MHz, CDCl$_3$) 1.52-1.61 (2H, m), 1.76-1.81 (2H, m), 2.20-2.26 (1H, m), 2.39 (2H, d, J=7.6 Hz), 2.40-2.50 (4H, m), 5.37 (1H, br), 5.51 (1H, br), 6.75-6.83 (1H, m), 7.01-7.08 (2H, m), 7.51 (2H, d, J=8.3 Hz) and 7.64 (2H, d, J=8.3 Hz).

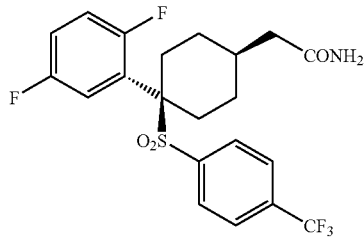

Example 43

Prepared from the acid of Example 42 by the procedure of Example 35, using ammonia in the second step. MS MH+462 (463).

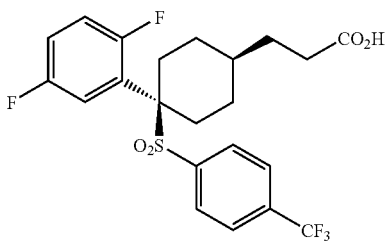 [SMILES: O=C(O)CC[C@H]1CC[C@@](c2cc(F)ccc2F)(S(=O)(=O)c2ccc(C(F)(F)F)cc2)CC1]

Example 44

Prepared from the ketone of Preparation 3, following the procedures of Preparations 5-8 and Examples 34, 37, 38 and 39.

$^1$H NMR (360 MHz, CDCl$_3$) δ 10.1 (1H, m), 7.64 (2H, d, J=8.3 Hz), 7.53 (2H, d, J=8.3 Hz), 7.09-7.00 (2H, m), 6.83-6.76 (1H, m), 2.50-2.37 (6H, m), 1.85-1.81 (2H, q, J=7.4 Hz), 1.75-1.70 (2H, m), 1.63-1.59) (1H, m), 1.55-1.45 (2H, m).
MS (EI$^+$) 477 (MH$^+$).

The invention claimed is:
1. A method of treating a cancer associated with modified Notch signaling in a mammal in need of such treatment comprising administering to said mammal a therapeutically effective amount of a compound of formula I:

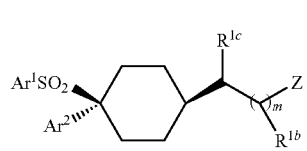

wherein:
m is 0 or 1;
Z represents CN, OR$^{2a}$, CO$_2$R$^{2a}$ or CON(R$^{2a}$)$_2$;
R$^{1b}$ represents H, C$_{1-4}$alkyl or OH;
R$^{1c}$ represents H or C$_{1-4}$alkyl,
Ar$^1$ represents phenyl or pyridyl, either of which bears 0-3 substituents independently selected from halogen, CN, NO$_2$, CF$_3$, OH, OCF$_3$, C$_{1-4}$-alkoxy or C$_{1-4}$alkyl which optionally bears a substituent selected from halogen, CN, NO$_2$, CF$_3$, OH and C$_{1-4}$alkoxy;
Ar$^2$ represents phenyl which is substituted in the 2- and 5-positions with halogen;
R$^{2a}$ represents H, C$_{1-6}$alkyl, C$_{3-6}$cycloalkyl, C$_{3-6}$cycloalkylC$_{1-6}$alkyl, C$_{2-6}$alkenyl, any of which optionally bears a substituent selected from halogen, CN, NO$_2$, CF$_3$, OR$^{2b}$, CO$_2$R$^{2b}$, N(R$^{2b}$)$_2$, CON(R$^{2b}$)$_2$, Ar and COAr; or R$^{2a}$ represents Ar; or two R$^{2a}$ groups together with a nitrogen atom to which they are mutually attached may complete an N-heterocyclyl group bearing 0-4 substituents independently selected from =O, =S, halogen, C$_{1-4}$alkyl, CN, NO$_2$, CF$_3$, OH, C$_{1-4}$alkoxy, C$_{1-4}$alkoxycarbonyl, CO$_2$H, amino, C$_{1-4}$alkylamino, di(C$_{1-4}$alkyl)amino, carbamoyl, Ar and COAr;
R$^{2b}$ represents H, C$_{1-6}$alkyl, C$_{3-6}$cycloalkyl, C$_{3-6}$cycloalkylC$_{1-6}$alkyl, C$_{2-6}$alkenyl, any of which optionally bears a substituent selected from halogen, CN, NO$_2$, CF$_3$, OH, C$_{1-4}$alkoxy, C alkoxycarbonyl, CO$_2$H, amino, C$_{1-4}$alkylamino, di(C$_{1-4}$alkyl)amino, carbamoyl, Ar and COAr; or R$^{2b}$ represents Ar; or two R$^{2b}$ groups together with a nitrogen atom to which they are mutually attached may complete an N-heterocyclyl group bearing 0-4 substituents independently selected from =O, =S, halogen, C$_{1-4}$alkyl, CN, NO$_2$, CF$_3$, OH, C$_{1-4}$alkoxy, C$_{1-4}$alkoxycarbonyl, CO$_2$H, amino, C$_{1-4}$alkylamino, di(C$_{1-4}$alkyl)amino, carbamoyl, Ar and COAr;
Ar represents phenyl or heteroaryl bearing 0-3 substituents selected from halogen, C$_{1-4}$alkyl, CN, NO$_2$, CF$_3$, OH, C$_{1-4}$alkoxy, C$_{1-4}$alkoxycarbonyl, amino, C$_{1-4}$alkylamino, di(C$_{1-4}$alkyl)amino, carbamoyl, C$_{1-4}$alkylcarbamoyl and di(C$_{1-4}$alkyl)carbamoyl;
or a pharmaceutically acceptable salt thereof.
2. The method according to claim 1 wherein Ar$^1$ is selected from phenyl groups substituted in the 4-position with halogen, methyl or trifluoromethyl, and phenyl groups substituted in the 3- and 4-positions by halogen.

3. The method according to claim 2 wherein $Ar^1$ is 4-chlorophenyl or 4-trifluoromethylphenyl and $Ar^2$ is 2,5-difluorophenyl.

4. The method according to claim 3 wherein m is 1, $R^{1b}$ and $R^{1c}$ both represent H, and Z represents $R^{2a}$.

5. The method according to claim 3 wherein m is 0, $R^{1c}$ represents H and Z represents $CON(R^{2a})_2$.

6. The method according to claim 4 wherein $R^{2a}$ represents H or $C_{1-6}$alkyl.

7. The method according to claim 1 wherein the cancer is selected from breast, prostate, colon, ovarian, colorectal and lung cancers.

8. The method according to claim 1 wherein the cancer is lymphoma or leukemia.

9. The method according to claim 8 wherein the cancer is T-ALL.

10. The method according to claim 1 wherein the compound of formula I is administered in combination with another anti-cancer agent or therapeutic agent, optionally in conjunction with radiation therapy.

11. The method according to claim 10 wherein said other anti-cancer agent or therapeutic agent is selected from the group consisting of: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, a γ-secretase and/or NOTCH inhibitor, an agent that interferes with receptor tyrosine kinases (RTKs), and an agent that interferes with a cell cycle checkpoint.

12. The method according to claim 1 wherein m is 1, Z represents $CO_2R^{2a}$, $R^{1b}$ represents H, $R^{1C}$ represents H, $Ar^1$ represents 4-chlorophenyl, $Ar^2$ represents 2,5-difluorophenyl, and $R^{2a}$ represents H.

* * * * *

UNITED STATES PATENT AND TRADEMARK OFFICE
CERTIFICATE OF CORRECTION

PATENT NO. : 8,362,075 B2  Page 1 of 1
APPLICATION NO. : 11/920445
DATED : January 29, 2013
INVENTOR(S) : Lewis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1472 days.

Signed and Sealed this
First Day of September, 2015

Michelle K. Lee
*Director of the United States Patent and Trademark Office*